United States Patent [19]

Handte et al.

[11] 4,383,850
[45] May 17, 1983

[54] BENZTHIAZOLE OR BENZOXAZOLE ETHERS, HERBICIDAL COMPOSITIONS AND USE

[75] Inventors: Reinhard Handte, Hofheim am Taunus; Klaus Bauer, Rodgau; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 367,882

[22] Filed: Apr. 13, 1982

[30] Foreign Application Priority Data

Apr. 15, 1981 [DE] Fed. Rep. of Germany ....... 3115152

[51] Int. Cl.³ .................. A01N 43/74; C07D 263/58; C07D 277/68
[52] U.S. Cl. .......................................... 71/88; 71/90; 71/92; 71/94; 71/95; 544/135; 544/137; 544/368; 546/198; 546/270; 548/159; 548/170; 548/221
[58] Field of Search ....................... 544/135, 137, 368; 546/198, 270; 548/170, 221, 159; 71/88, 90, 94, 95, 92

[56] References Cited

PUBLICATIONS

Handte et al. *Chemical Abstracts*, vol. 88, No. 190816h, (1978).

*Primary Examiner*—Robert W. Ramsuer
*Attorney, Agent, or Firm*—Curtis, Morris & Safford

[57] ABSTRACT

Compounds of the formula

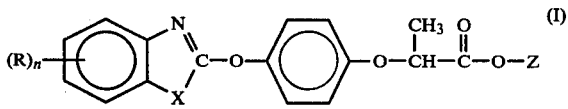

in which R denotes halogen, $CF_3$, $NO_2$ or CN, n denotes 0-2, X denotes O or S and Z denotes radicals of the formulae

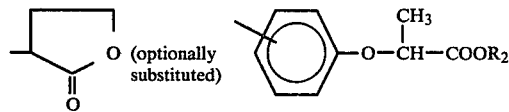

or $-C_pH_{2p}-R_3$ (in which, inter alia, $R_3$ can be a heterocyclic radical), are valuable herbicides, particularly against monocotyledonous weeds.

8 Claims, No Drawings

BENZTHIAZOLE OR BENZOXAZOLE ETHERS, HERBICIDAL COMPOSITIONS AND USE

The present invention relates to new 4-oxyphenoxyalkanecarboxylic acid derivatives, containing heterocyclic substituents, of the general formula I

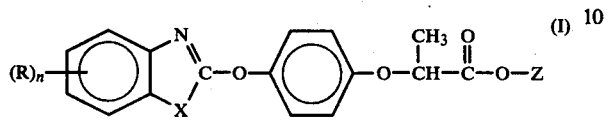

in which R denotes halogen, $CF_3$, $NO_2$ or CN, n denotes 0, 1 or 2, X denotes O, or S and Z denotes a group of the formulae

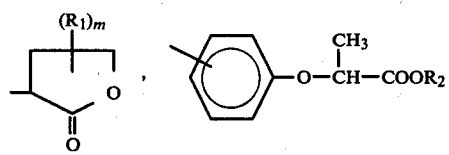

or $-C_pH_{2p}-R_3$, $R_1$ denotes $(C_1-C_4)$-alkyl or phenyl, m denotes 0–2, p denotes 1 or 2, $R_2$ denotes H, $(C_1-C_4)$-alkyl or a cation equivalent, and $R_3$ denotes any desired 3-membered to 7-membered heterocyclic ring system having up to three hetero-atoms which is optionally monosubstituted or disubstituted by $(C_1-C_4)$-alkyl and/or contains oxo groups and which can also contain a fused benzene ring.

Preferred compounds of the general formula I are those in which R is halogen (especially F, Cl or Br) or $CF_3$ and n is zero or 1 and Z has the meaning indicated.

The following are possible examples of heterocyclic ring systems in the $R_3$ position:

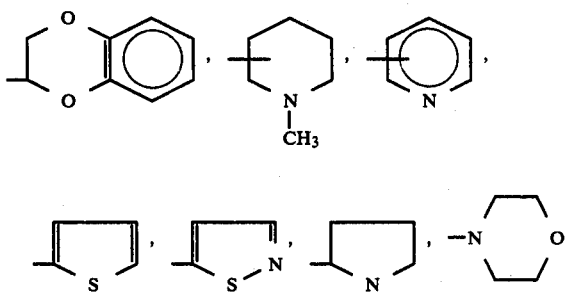

Cation equivalents in the $R_2$ position are preferably $Na^+$ and $K^+$.

The compounds of the general formula I possess a centre of asymmetry and are usually obtained in the form of racemates when they are prepared. However, the invention also covers the isolated optical antipodes and, in this respect, especially their D-forms.

The invention also relates to a process for the preparation of the compounds of the formula I which comprises (a) reacting compounds of the formula

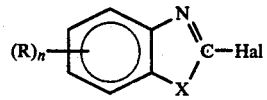

in which Hal represents a halogen atom, with compounds of the formula

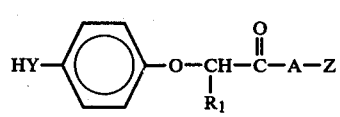

or (b) reacting compounds of the formula

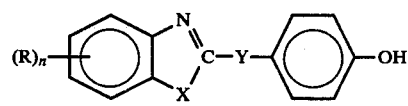

with compounds of the formula

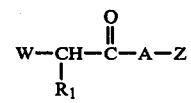

in which W represents halogen (preferably chlorine or bromine) or the tosyl radical, or (c) reacting compounds of the formula

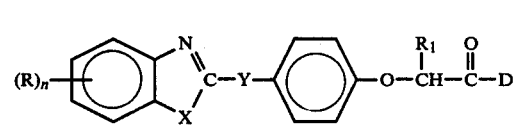

with compounds of the formula B—Z (VII), in every case one of the radicals D and B representing halogen and the other representing the group —AH.

The reactions specified in (a) and (c) are carried out in a manner with which the expert is conversant, and are either carried out in the presence of acid-binding agents or the starting materials III, IV or VI (VII) are employed in the form of their salts, which can, if appropriate, be produced in situ. The general processes are described in greater detail in, for example, U.S. Pat. No. 4,130,413.

The starting compounds of the formulae II–VII are known or can be prepared by known processes. If optically active starting materials of the formulae III, V or VI are used, it is possible to prepare optical isomers of the compounds according to the invention (preferably the D-form) of the general formula I in a high state of optical purity.

The compounds, according to the invention, of the general formula I are very effective in the pre-emergence and post-emergence processes against a broad spectrum of annual and perennial gramineous weeds, but, at the same time, they are tolerated excellently by dicotyledonous crop plants and by some species of cereals. The compounds are therefore suitable for selectively combating annual and perennial gramineous weeds in crop plants. Examples of such gramineous weeds are wild oats (Avena), foxtail (Alopecurus spp.), meadow-grass (Poa spp.), rye grass (Lolium spp.), annual and perennial wild millet (Echinochloa spp., Setaria spp., Digitaria spp., Panicum spp. and Sorghum spp.), Bermuda grass (Cynodon spp.) and couch-grass (Agropyron spp.).

The present invention also relates, therefore, to herbicidal agents which contain a herbicidally effective quantity of a compound of the general formula I as well as customary additives and formulation aids.

The agents according to the invention generally contain 2–95% by weight of the active compounds of the formula I. They can be applied in the customary formulations as wettable powders, emulsifiable concentrates, atomizable solutions, dusting agents or granules.

Wettable powders are preparations which can be dispersed uniformly in water and which, besides the active compound and a diluent or inert substance, also contain wetting agents, for example polyoxethylated alkylphenols, polyoxethylated oleylamines, stearylamines, alkylsulfonates or alkylphenylsulfonates, and dispersing agents, for example sodium ligninsulfonate, sodium 2,2′-dinaphthylmethane-6,6′-disulfonate or sodium oleylmethyltauride.

Emulsifiable concentrates are obtained by dissolving the active compound in an organic solvent, for example butanol, cyclohexanone, dimethylformamide, xylene or higher-boiling aromatic fractions, and adding a non-ionic wetting agent, for example a polyoxethylated alkylphenol or a polyoxethylated oleylamine or stearylamine.

Dusting agents are obtained by grinding the active compound with finely divided solid substances, for example talc, natural clays, such as kaolin, bentonite or pyrophillite, or diatomaceous earth.

Granules can be prepared either by atomizing the active compound onto an adsorbent, granulated inert material or by applying active compound concentrates to the surface of carriers, such as sand, kaolinite or granulated inert material, by means of adhesives, for example polyvinyl alcohol, sodium polyacrylate or mineral oils. Suitable active compounds can also be prepared in the manner customary for the production of fertilizer granules—if desired as a mixture with fertilizers.

The concentrations of the active compounds for the herbicidal agents can vary in the commercially available formulations. In wettable powders the concentration of active compound varies, for example, between about 10% and 95%, the remainder comprising the formulation additives indicated above. For emulsifiable concentrates the concentration of active compound is about 10% to 80%. Formulations in the form of dust in most cases contain 5% to 20% of active compound. For granules the content of active compound depends in part on whether the active compound is in a liquid or solid form and on the granulating auxiliaries, fillers and the like which are used.

For application, the commercially available concentrates are, if appropriate, diluted in a customary manner, for example by means of water in the case of wettable powders and emulsifiable concentrates. Formulations in the form of dust and granulated formulations and also atomizable solutions are not diluted further with additional inert substances before application. The application rate required varies with the external conditions such as temperature, humidity and other factors. It can vary within wide limits, for example between 0.5 and 10.0 kg/hectare or more of active substance, but is preferably between 0.1 and 5 kg/hectare.

The active compounds according to the invention can be combined with other herbicides, insecticides and fungicides.

Preparations which are particularly suitable when the active compounds are combined with herbicides are the preparations which are effective against dicotyledons and belong to the group comprising nitrodiphenyl ethers and phenmedipham, desmedipham, bentazon, metamitron and the following urea

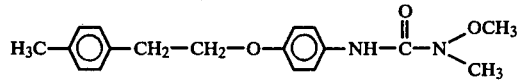

FORMULATION EXAMPLES

Example A

An emulsifiable concentrate is obtained from 15 parts by weight of active compound, 75 parts by weight of cyclohexanone, as solvent, and 10 parts by weight of oxethylated nonylphenol (10 EO) as emulsifier.

Example B

A wettable powder which can easily be dispersed in water is obtained by mixing, and grinding in a pin disk mill, 25 parts by weight of active compound, 64 parts by weight of kaolin-containing quartz, as inert material, 10 parts by weight of potassium ligninsulfonate and 1 part by weight of sodium oleylmethyltauride, as wetting agent and dispersing agent.

Example C

A dusting agent is obtained by mixing, and comminuting in a beater mill, 10 parts by weight of active compound and 90 parts by weight of talc, as inert material.

Example D

Granules are composed, for example, of about 2–15 parts by weight of active compound and 98–85 parts by weight of inert granular materials, such as, for example attapulgite, pumice stone and quartz sand.

PREPARATION EXAMPLES

Example 1

2-Oxotetrahydrofuran-3-yl 2-[4-(6-chloro-2-benzthiazolyloxy)-phenoxy]-propanoate 21 g (0.06 mole) of 2-[4-(6-chloro-2-benzthiazolyloxy)-phenoxy]-propionic acid were initially taken together with 10.4 g (0.075 mole) of potassium carbonate in 100 ml of acetone and the mixture was stirred for approx. ½ hour at 45° C., a thick paste being formed. 11.6 g (0.07 mole) of 2-bromobutyrolactone in 50 ml of acetone were then added dropwise in the course of ½ hour. When the addition was complete, the reaction mixture became highly fluid; the conversion was followed by means of thin-layer chromatography and was approx. 70% after 5 hours. Altogether, the mixture was stirred for 16 hours at approx. 50° C. After cooling, the salt was filtered off, the acetone was removed by distillation and the residue was taken up in approx. 200 ml of toluene and washed with water and saturated sodium bicarbonate solution. After drying, the toluene was removed by distillation and the residue remaining was dried in vacuo (0.05 mbar) for one hour at approx. 70° C. The product remaining after drying was 22 g (91.3% of theory) of a very viscous oil, which was identified by $^1$H nuclear magnetic resonance spectroscopy as 2-oxotetrahydrofuran-3-yl 2-[4-(6-benzthiazolyloxy)-phenoxy]-propanoate.

gave a solution of the product in toluene, which was separated off. Removing the toluene by distillation gave a viscous residue, which was dried for one hour at 100° C. in vacuo (0.05 mbar). After drying, 40.4 g (89.8% of theory) of 2-morpholinoethyl 2-[4-(6-chloro-2-benzthiazolyloxy)-phenoxy]-propanoate were obtained in the form of a viscous oil. The structure of the compound was proved with the aid of $^1$H nuclear magnetic resonance spectroscopy.

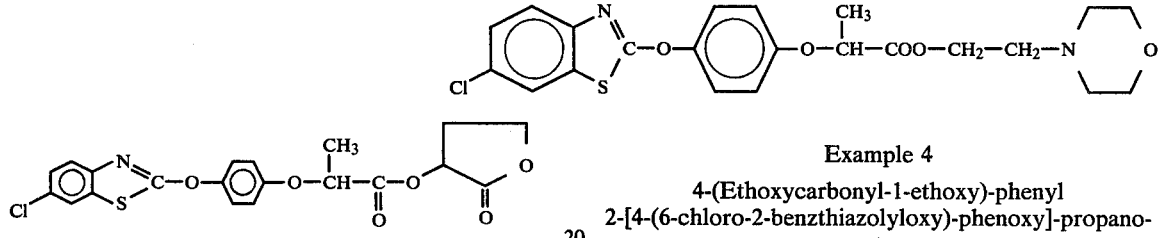

Example 2

(D+)-2-Oxotetrahydrofuran-3-yl 2-[4-(6-chloro-2-benzthiazolyloxy)-phenoxy]-propanoate Using a procedure analogous to that of Example 1, but employing the D-form of the acid instead of the racemate, (D+)-2-oxotetrahydrofuran-3-yl 2-[4-(6-chloro-2-benzthiazolyloxy)-phenoxy]-propanoate was obtained in the same yield. It was identified by $^1$H nuclear magnetic resonance spectroscopy and by measuring the angle of rotation in chloroform.

Example 4

4-(Ethoxycarbonyl-1-ethoxy)-phenyl 2-[4-(6-chloro-2-benzthiazolyloxy)-phenoxy]-propanoate 17.5 g (0.05 mole) of 2-[4-(6-chloro-2-benzthiazolyloxy)-phenoxy]-propionic acid were dissolved in 100 ml of dry toluene and converted into the acid chloride by warming with 7.15 g (0.06 mole) of thionyl chloride. After removing excess thionyl chloride and approx. 50 ml of toluene by distillation, 10.5 g (0.05 mole) of ethyl-2-(4-hydroxyphenoxy) propanoate and 6.1 g (0.06 mole) of triethylamine in 100 ml of toluene were added dropwise. When the addition was complete, the mixture was stirred for 1 hour at 50° C. and cooled. The reaction product was washed with twice 50 ml of 5% strength sodium hydroxide solution and with twice 100 ml of water. When the product had been dried and concentrated, 26 g (96% of theory) of 4-(ethoxycarbonyl-1-ethoxy)-phenyl 2-[4-(6-chloro-2-benzthiazolyloxy)-phenoxy]-propanoate were left as an oily residue. Identification was effected by means of $^1$H nuclear magnetic resonance spectroscopy.

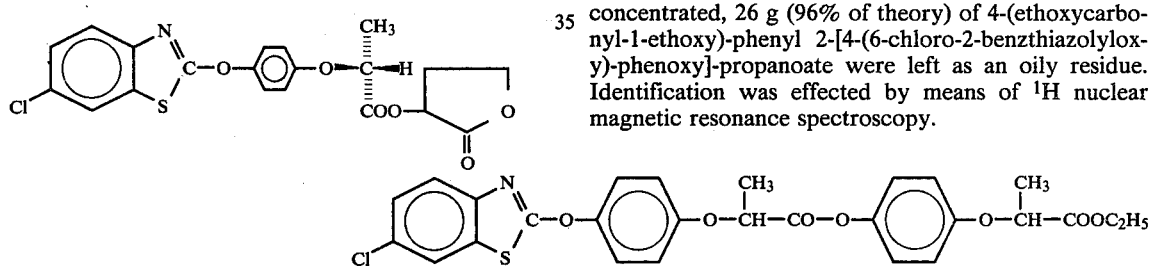

Example 3

2-Morpholinoethyl 2-[4-(6-chloro-2-benzthiazolyloxy)-phenoxy]-propanoate 35 g (0.1 mole) of 2-[4-(6-chloro-2-benzthiazolyloxy)-phenoxy]-propionic acid were suspended in 250 ml of dry toluene, and 14.3 g (0.12 mole) of thionyl chloride, diluted with 50 ml of toluene, were added at 60° C. in the course of 1 hour. When the addition was complete, the mixture was stirred for a total of 7 hours at 70° C. and excess thionyl chloride was then removed by distillation with approx. 100 ml of toluene, giving a clear solution of the acid chloride. The mixture was cooled, 100 ml of dry toluene were added, followed by 12 g (0.1 mole) of morpholinoethanol, dissolved in 100 ml of toluene, and, when the addition was complete the mixture was stirred for 1 hour at 50° C., giving initially the hydrochloride of the compound; adding 200 ml of saturated bicarbonate solution and then washing with water It was possible to prepare the following compounds analogously to the preceding examples.

| Serial No. | (R)$_n$ | X | Z | Melting point boiling point, [n$_D$] |
|---|---|---|---|---|
| 5 | 6-Cl | O | ![structure]—O—CH(CH$_3$)—COOC$_2$H$_5$ | $^1$H NMR Spectrum (Table 2) |
| 6 | 6-F | S | —CH$_2$—CH$_2$—N(morpholino) | |
| 7 | 6-Br | S | —CH$_2$—CH$_2$—N(2-oxopiperidyl) | |

-continued

| Serial No. | (R)$_n$ | X | Z | Melting point boiling point, [n$_D$] |
|---|---|---|---|---|
| 8 | 5-Cl | O | —CH$_2$—CH$_2$—N⟨piperidine⟩ | |
| 9 | 6-Cl | O | —CH$_2$—CH—CH$_2$ with O—C(CH$_3$)$_2$—O (dioxolane) | |
| 10 | 6-Cl | S | —CH$_2$—CH$_2$—(pyridyl) | |
| 11 | 6-Cl | S | —CH$_2$—CH—CH$_2$ with O—C(CH$_3$)$_2$—O (dioxolane) | |
| 12 | 6-Cl | S | —CH$_2$—CH$_2$—N⟨morpholine⟩ | |
| 13 | 6-Cl | O | —CH$_2$—CH$_2$—N⟨N-methylpiperazine⟩—N—CH$_3$ | |

TABLE 2

$^1$H NMR data for characterizing individual compounds from the series of preparation examples, recorded at 60 MHz, solvent CDCL$_3$; chemical shift ∂ (ppm) relative to the standard TMS (in brackets: the multiplicity and relative intensity of the signals)

| Example No. | —CH$_3$ | —CH$_2$— | —CH— | Aromatic structures |
|---|---|---|---|---|
| 1 and 2 | 1.65 (d) | 2.9–2 (m) 4.9–4.2 (m) | 4.8 (q) 4.4 (t) | 6.6–7.2 (m, 7) |
| 4 | 1.2 (t) 1.65 (d) 1.75 (d) | 4.2 (q) | 4.65 (q) 4.9 (q) | 6.6–7.8 (m, 11) |
| 5 | 1.2 (t) 1.6 (d) | 4.2 (q) | 4.7 (q) 4.9 (q) | 6.65–7.6 (m, 11) |
| | 1.75 (d) | | | | d = doublet
t = triplet
q = quadruplet
m = multiplet

BIOLOGICAL EXAMPLES

Example I

Pre-emergence treatment

The seeds of grasses were sown in pots and the preparations according to the invention, which had been formulated as wettable powders or as emulsion concentrates, were sprayed onto the surface of the soil at various dosage rates. The pots were then placed in a greenhouse for 4 weeks and the result of the treatment (as in the case of the following examples, too) was established by an assessment in accordance with the rating which follows (see table).

The preparations according to the invention exhibited a good action against annual and, in some cases, also perennial gramineous weeds:

| Example | Dose of a.i./ hectare | AVF | ALM | SAL | LOM | ECG | AGR | CND |
|---|---|---|---|---|---|---|---|---|
| 1 | 2.4 kg | 5 | 5 | 5 | 5 | 5 | 5 | 5 |
| | 0.6 kg | 5 | 5 | 5 | 5 | 5 | — | — |
| 4 | 2.4 kg | 5 | 5 | 5 | 5 | 5 | 5 | — |
| | | 5 | 5 | 5 | 5 | 5 | — | — |
| 5 | 2.4 kg | 5 | 5 | 5 | 5 | 5 | — | — |
| | 0.6 kg | 4 | 4 | 5 | 4 | 5 | — | — |

AVF: wild oats
ALM: slender foxtail
SAL: bristle-grass
LOM: rye grass
ECG: cockspur grass
AGR: couch-grass
CND: Bermuda grass
a.i. = active ingredient

Example II

Post-emergence treatment

The seeds of grasses were sown in pots and cultivated in a greenhouse. 3 weeks after sowing, the preparations according to the invention, which had been formulated as wettable powders or an emulsion concentrates, were sprayed onto the plants at various dosage rates, and the action of the preparation was assessed after a waiting period of 4 weeks in a greenhouse.

The agents according to the invention had a good action against a broad spectrum of annual gramineous weeds. Furthermore, some preparations also combated the perennial gramineous weeds Cynodon dactylon, Sorghum halepense and Agropyron repens; Patent example 1 may be mentioned in this connection.

| Dose | AVF | ALM | SAL | LOM | ECG | AGR | CND |
|---|---|---|---|---|---|---|---|
| 2.4 kg of a.i./kg | 5 | 5 | 5 | 5 | 5 | 5 | — |

| Dose | AVF | ALM | SAL | LOM | ECG | AGR | CND |
|---|---|---|---|---|---|---|---|
| 0.6 kg of a.i./kg | 5 | 5 | 5 | 5 | 5 | — | — |

Example III

Compatibility with crop plants

In further greenhouse tests, seeds of a fairly large number of crop plants were laid out in pots. Some of the pots were treated immediately, the remainder were placed in a greenhouse until the plants had developed 2 to 3 true leaves and were then sprayed with substances according to the invention.

The results were determined 4 to 5 weeks after application and show that, even at a rate of 2.5 kg/hectare, the substances according to the invention leave dicotyledonous crops completely, or almost completely, unharmed in the pre-emergence and post-emergence techniques. In addition, some substances also leave unharmed gramineous crops, such as barley, sorghum, corn, wheat or rice. The substances are thus highly selective in regard to the weed-killing action described in the previous examples.

TABLE

| Assessment in % and figures | |
|---|---|
| Assessment figure | % harmful effect on weeds and crop plants |
| 1 | 0–20% |
| 2 | 20–40% |
| 3 | 40–60% |
| 4 | 60–80% |
| 5 | 80–100% |

We claim:

1. A compound of the formula I

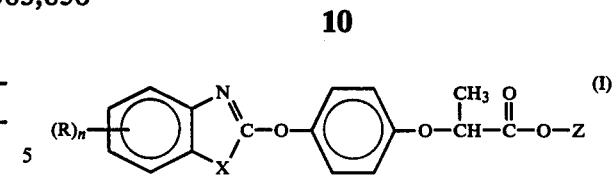

in which R denotes halogen, $CF_3$, $NO_2$ or CN, n denotes 0, 1 or 2, X denotes O or S and Z denotes a group of the formulae

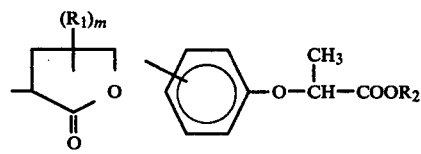

or $-C_pH_{2p}-R_3$, $R_1$ denotes $(C_1-C_4)$-alkyl or phenyl, m denotes 0–2, p denotes 1 or 2, $R_2$ denotes H, $(C_1-C_4)$-alkyl or a cation equivalent, and $R_3$ denotes a 3-membered to 7-membered heterocyclic ring system having up to three hetero-atoms which is optionally monosubstituted or disubstituted by $(C_1-C_4)$-alkyl and/or contains oxo groups and which can also contain a fused benzene ring.

2. The compound of claim 1 which is 2-oxotetrahydrofuran-3-yl-2-[4-(6-chloro-2-benzthiazolyloxy)-phenoxy]-propanoate.

3. The compound of claim 1 which is (D+)-2-oxotetrahydrofuran-3-yl-2-[4-(6-chloro-2-benzthiazolyloxy)-phenoxy]-propanoate.

4. The compound of claim 1 which is 2-morpholinoethyl 2-[4-(6-chloro-2-benzthiazolyloxy)-phenoxy]-propanoate.

5. The compound of claim 1 which is 4-(ethoxycarbonyl-1-ethoxy)-phenyl-2-[4-(6-chloro-2-benzthiazolyloxy)-phenoxy]-propanoate.

6. The compound of claim 1 which is 4-(ethoxycarbonyl-1-ethoxy)-phenyl-2-[4-(6-chloro-2-benzoxazolyloxy)-phenoxy]-propanoate.

7. A herbicidal composition which contains a compound of claim 1 in association with a carrier.

8. A process for combating undesirable grasses in crop plants, which comprises applying a herbicidally effective quantity of a compound of the formula I to the undesirable grasses or to their habitat.

* * * * *